(12) United States Patent
Kapczynski

(10) Patent No.: US 7,794,714 B2
(45) Date of Patent: Sep. 14, 2010

(54) NEWCASTLE DISEASE VIRUS MONOCLONAL ANTIBODIES

(75) Inventor: Darrell R. Kapczynski, Bishop, GA (US)

(73) Assignee: The United States of America as represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 12/075,920

(22) Filed: Mar. 14, 2008

(65) Prior Publication Data

US 2009/0232845 A1    Sep. 17, 2009

(51) Int. Cl.
*A61K 39/395* (2006.01)
(52) U.S. Cl. .................................... 424/130.1; 435/345
(58) Field of Classification Search ............... 424/130.1; 435/345; 530/300
See application file for complete search history.

(56) References Cited

OTHER PUBLICATIONS

Erdei et al, Arch. of Virology, 1987, vol. 96, pp. 265-269.*
Long et al, Journal of Virology, 1986, vol. 57, No. 3, pp. 1198-1220.*
Iorio et al, Journal of Virology, 1983, vol. 48, No. 2, pp. 440-450.*
Russell et al, Journal of General Virology, 1983, vol. 64, pp. 2069-2072.*

* cited by examiner

*Primary Examiner*—Ali R. Salimi
(74) *Attorney, Agent, or Firm*—John D. Fado; Gall E. Poulos

(57) ABSTRACT

Anti-peptide monoclonal antibodies (MAb's) specific for Exotic Newcastle Disease (END) are used for rapid diagnostic identification between poultry infected with vaccine strains of NDV (LaSota/B1) and END virus (ENDV). Exotic Newcastle Disease is a contagious and fatal viral disease of birds and poultry. The present invention provides for diagnostic detection of ENDV in commercial poultry.

4 Claims, 5 Drawing Sheets

| | | |
|---|---|---|
| Majority | MDRAVSQVALENDEREAKNTWRLIFRIAILLLTVVTLAISVASLVYSMGASTPSDLVGIPTRISRAEEKITSALGSNQDV | |
| | 10        20        30        40        50        60        70        80 | |
| CA02 HN.pro | MDRVVSRVVLENEEREAKNTWRLVFRVAVLSLIVMTLAISVAALVYSMEASTPNDLAGISTVISRAEDRVTSLLNSNQDV | 80 |
| Lasota46.pro | MDRAVSQVALENDEREAKNTWRLIFRIAILFLTVVTLAISVASLLYSMGASTPSDLVGIPTRISRAEEKITSTLGSNQDV | 80 |
| Texas GB.pro | MDRAVSQVALENDEREAKNTWRLIFRIAILLLTVVTLATSVASLVYSMGASTPSDLVGIPTRISRAEEKITSALGSNQDV | 80 |
| hertz 33.pro | MDRAVSRVALENEEREAKNTWRFVFRIAILLLIVITLAISAAALVYSMEASTPGDLVGIPTVISRAEEKITSALSSNQDV | 80 |
| Roakin.pro | MDRTVSQVALENDEREAKNTWRLIFRIAILLLTVVTLATSVASLVYSMGASTPSDLVGIPTRISRAEEKITSALGSNQDV | 80 |
| Majority | VDRIYKQVALESPLALLNTETTIMNAITSLSYQINGAANNSGWGAPIHDPDYIGGIGKELIVDDASDVTSFYPSAFQEHL | |
| | 90       100       110       120       130       140       150       160 | |
| CA02 HN.pro | VDRVYKQVALESPLALLNTESIIMNAITSLSYQINGAANSSGCGAPVHDPDYIGGVGKELIVDDTSDATSFYPSAYQEHL | 160 |
| Lasota46.pro | VDRIYKQVALESPLALLKTETTIMNAITSLSYQINGAANNSGWGAPIHDPDYIGGIGKELIVDDASDVTSFYPSAFQEHH | 160 |
| Texas GB.pro | VDRIYKQVALESPLALLNTETTIMNAITSLSYQINGAANNSGWGAPIHDPDFIGGIGKELIVDDASDVTSFYPSAFQEHL | 160 |
| hertz 33.pro | VDRIYKQVALESPLALLNTESVIMNAITSLSYQINGAANNSGCGAPVHDPDYIGGIGKELIVDDASDVTSFYPSAFQEHL | 160 |
| Roakin.pro | VDRIYKQVALESPLALLNTETTIMNAITSLSYQINGAANNSGWGAPIHDPDFIGGIGKELIVDDASDVTSFYPSAFQEHL | 160 |
| Majority | NFIPAPTTGSGCTRIPSFDMSATHYCYTHNVILSGCRDHSHSYQYLALGVLRTSATGRVFFSTLRSINLDDTQNRKSCSV | |
| | 170       180       190       200       210       220       230       240 | |
| CA02 HN.pro | NFIPAPTTGSGCTRIPSFDMSATHYCYTHNVILSGCRDHSHSHQYLALGVLRTSATGRVFFSTLRSINLDDTQNRKSCSV | 240 |
| Lasota46.pro | NFIPAPTTGSGCTRIPSFDMSATHYCYTHNVILSGCRDHSHSYQYLALGVLRTSATGRVFFSTLRSINLDDTQNRKSCSV | 240 |
| Texas GB.pro | NFIPAPTTGSGCIRIPSFDMSATHYCYTHNIISSGCRDHSHSYQYLALGVLRTSATGRIFFSTLRSINLDDTQNRKSCSV | 240 |
| hertz 33.pro | NFIPAPTTGSGCTRIPSFDISATHYCYTHNVILSGCRDHSHSHQYLALGVLRTSATGRVFFSTLRSINLDDNQNRKSCSV | 240 |
| Roakin.pro | NFIPAPTTGSGCIRIPSFDMSATHYCYTHNIISSGCRDHSHSYQYLALGVLRTSATGRIFFSTLRSINLDDTQNRKSCSV | 240 |
| Majority | SATPLGCDMLCSKVTETEEEDYNSAVPTLMVHGRLGFDGQYHEKDLDVTTLFEDWVANYPGVGGGSFIDSRVWFSVYGGL | |
| | 250       260       270       280       290       300       310       320 | |
| CA02 HN.pro | SATPLGCDMLCSKVTETEEEDYKSVTPTSMVHGRLGFDGQYHEKDLDVTVLFKDWVANYPGVGGGSLIDDRVWFPVYGGL | 320 |
| Lasota46.pro | SATPLGCDMLCSKVTETEEEDYNSAVPTRMAHGRLGFDGQYHEKDLDVTTLFGDWVANYPGVGGGSFIDSRVWFSVYGGL | 320 |
| Texas GB.pro | SATPLGCDMLCSKVTETEEEDYNSAVPTLMVHGRLGFDGQYHEKDLDVTTLFEDWVANYPGVGGGSFIDSRVWFSVYGGL | 320 |
| hertz 33.pro | SATPLGCDMLCSKITETEEEDYSSVTPTSMVHGRLGFDGQYHEKDLDVITLFKDWVANYPGVGGGSFIDNRVWFPVYGGL | 320 |
| Roakin.pro | SATPLGCDMLCSKVTETEEEDYNSAVPTLMVHGRLGFDGQYHEKDLDVTTLFEDWVANYPGVGGGSFIDSRVWFSVYGGL | 320 |
| Majority | KPNSPSDTVQEGKYVIYKRYNDTCPDEQDYQIRMAKSSYKPGRFGGKRIQQAILSIKVSTSLGEDPVLTVPPNTVTLMGA | |
| | 330       340       350       360       370       380       390       400 | |
| CA02 HN.pro | KPNSPSDTAQEGKYVIYKRYNNTCPDEQDYQVRMAKSSYKPGRFGGKRVQQAILSIKVSTSLGEDPVLTVPPNTVTLMGA | 400 |
| Lasota46.pro | KPNSPSDTVQEGKYVIYKRYNDTCPDEQDYQIRMAKSSYKPGRFGGKRIQQAILSIKVSTSLGEDPVLTVPPNTVTLMGA | 400 |
| Texas GB.pro | KPNSPSDTVQEEKYVIYKRYNDTCPDEQDYQIRMAKSSYKPGRFGGKRIQQAILSIKVSTSLGEDPVLTVPPNTVTLMGA | 400 |
| hertz 33.pro | KPNSPSDTVQEGKYVIYKRYNDTCPDEQDYQIRMAKSSYKPGRFGGKRVQQAILSIKVSTSLGEDPVLTIPPNTVTLMGA | 400 |
| Roakin.pro | KPNSPSDTVQEEKYVIYKRYNDTCPDEQDYQIRMAKSSYKPGRFGGKRIQQAILSIKVSTSLGEDPVLTVPPNTVTLMGA | 400 |
| Majority | EGRILTVGTSHFLYQRGSSYFSPALLYPMTVSNKTATLHSPYTFNAFTRPGSIPCQASARCPNSCVTGVYTDPYPLIFYR | |
| | 410       420       430       440       450       460       470       480 | |
| CA02 HN.pro | EGRILTVGTSHFLYQRGSSYFSPALLYPMTVRNKTATLHSPYTFNAFTRPGSVPCQASARCPNSCITGVYTDPYPVVFHR | 480 |
| Lasota46.pro | EGRILTVGTSHFLYQRGSSYFSPALLYPMTVSNKTATLHSPYTFNAFTRPGSIPCQASARCPNPCVTGVYTDPYPLIFYR | 480 |
| Texas GB.pro | EGRILTVGTSHFLYQRGSSYFSPALLYPMTVSNKTATLHSPYTFNAFTRPGSIPCQASARCPNSCVTGVYTDPYPLIFYR | 480 |
| hertz 33.pro | EGRVLTVGTSHFLYQRGSSYFSPALLYPMTVNNKTATLHSPYTFNAFTRPGSVPCQASARCPNSCVTGVYTDPYPLIFHR | 480 |
| Roakin.pro | EGRILTVGTSHFLYQRGSSYFSPALLYPMTVSNKTATLHSPYTFNAFTRPGSIPCQASARCPNSCVTGVYTDPYPLIFYR | 480 |
| Majority | NHTLRGVFGTMLDGEQARLNPASAVFDSTSRSRITRVSSSSTKAAYTTSTCFKVVKTNKTYCLSIAEISNTLFGEFRIVP | |
| | 490       500       510       520       530       540       550       560 | |
| CA02 HN.pro | NHTLRGVFGTMLDNEQARLNPVSAIFDYTSRSRITRVSSTSTKAAYTTSTCFKVVKTNKVYCLSIAEISNTLFGEFRIVP | 560 |
| Lasota46.pro | NHTLRGVFGTMLDGVQARLNPASAVFDSTSRSRITRVSSSSTKAAYTTSTCFKVVKTNKTYCLSIAEISNTLFGEFRIVP | 560 |
| Texas GB.pro | NHTLRGVFGTMLDGEQARLNPASAVFDSTSRSRITRVSSSSTKAAYTTSTCFKVVKTNKTYCLSIAEISNTLFGEFRIVP | 560 |
| hertz 33.pro | NHTLRGVFGTMLDDGQARLNPVSAVFDNISRSRITRVSSSRTKAAYTTSTCFKVVKTNKTYVLSIAEISNTLFGEFRIVP | 560 |
| Roakin.pro | NHTLRGVFGTMLDGEQARLNPASAVFDSTSRSRITRVSSSSTKAAYTTSTCFKVVKTNKTYCLSIAEISNTLFGEFRIVP | 560 |
| Majority | LLVEILKNDGVREARSG | |
| | 570 | |
| CA02 HN.pro | LLVEILKDDRV | SEQ ID NO. 8 | 571 |
| Lasota46.pro | LLVEILKDDGVREARSG | SEQ ID NO. 9 | 577 |
| Texas GB.pro | LLVEILKNDGVREARSG | SEQ ID NO. 10 | 577 |
| hertz 33.pro | LLVEILKNDGV | SEQ ID NO. 11 | 571 |
| Roakin.pro | LLVEILKNDGVREARSG | SEQ ID NO. 12 | 577 |

Figure 2

```
Majority      QTTPHDSPPATSADQPPTQATDEAVDTQLRTGASNSLLLMLDKLSNKSSNAKKGPWSSPQEGNHQRPTQQQGSQPSRGNS
                     90        100       110       120       130       140       150       160
LaSota46.pro  ............................................................................... 160
B1 P.pro      ............................................................................... 160
Ca02.pro      .A.S.N..S..P.ES.....AG..G....K........S............T...SR....G.H..PLAK.H.N.LNH..H 160   SEQ ID No. 13
```

Figure 3

Peptide seq #

7F8

10F11

13F7

Peptide seq #

NEWCASTLE DISEASE VIRUS MONOCLONAL ANTIBODIES

BACKGROUND OF THE INVENTION

1. Field of the Invention

This invention relates to monoclonal antibodies, the hybridomas producing the antibodies, and methods for identifying and distinguishing vaccine strains of Newcastle disease virus from highly virulent Exotic Newcastle Disease virus. It also relates to peptides used to make the monoclonal antibodies.

2. Description of the Related Art

Newcastle disease virus (NDV), a member of the Paramyxoviridae family, is designated avian paramyxovirus 1. The enveloped virus has a negative-sense single-stranded genome of approximately 15 kb which codes for six proteins, including an RNA-directed RNA polymerase, hemaglutinin-neuraminidase protein, fusion protein, matrix protein, phosphoprotein, and nucleocapsid protein (Alexander, In: B. W. Calnek, H. J. Barnes, C. W. Beard, W. M. Reid, and H. W. Yoder, Jr (Eds), Diseases of Poultry, 9$^{th}$ ed., Iowa State University Press, Ames, Iowa, p. 496-519, 1991). Outbreaks of Newcastle disease were first reported for poultry from Java, Indonesia, and Newcastle-upon-Tyne, England in 1926. The disease currently has a worldwide distribution with a wide host range in which all orders of birds have been reported to be infected by NDV. Infectious virus may be ingested or inhaled, which results in its transmission and is the basis for mass-application vaccination procedures for poultry (Diseases of Poultry, 1991, supra). Isolates of NDV are categorized into three main pathotypes depending on the severity of disease produced by the isolate in chickens (Alexander, In: H. G. Purchase, L. H. Arp, C. H. Domermuth, and J. E. Pearson (Eds.), A Laboratory Manual for the Isolation and Identification of Avian Pathogens, 3$^{rd}$ edition, American Association of Avian Pathologists, Inc., Kennet Square, Pa.; 114-120, 1989; Alexander, 1991, supra). Lentogenic isolates do not usually cause disease in adult birds and are considered avirulent. Viruses of intermediate virulence that cause respiratory disease are termed mesogenic, while virulent viruses that cause high mortality are termed velogenic. In the United States, disease outbreaks of velogenic NDV in poultry are also termed Exotic New Castle Disease (END) and isolates from those outbreaks are termed END Virus (ENDV). Neurotropic and viscerotropic forms of velogenic viruses have been reported worldwide (Alexander, 1991, supra). Viscerotropic velogenic viruses have entered the United States via importation of psittacines (Bruning-Fann et al., J. Am. Vet. Med. Assoc., Volume 201, 1709-1714, 1992; Panigraphy et al., Avian Dis., Volume 37, 254-258, 1993; Senne et al., Avian Dis., Volume 27, 731-744, 1983) and were the causal agent of the major outbreak in southern California during the early 1970s (Schloer, ILnfect. Immun., Volume 10, 724-732, 1968; Utterback and Schwartz, J. Am. Vet. Med. Assoc., Volume 163, 1080-1088, 1973). Outbreaks of Newcastle disease in cormorants in the north central United States and southern Canada in the 1990s were attributed to neurotropic velogenic viruses (Bannerjee et al., Avian Dis., Volume 38, 873-878, 1994; Wobeser et al., Can. Vet. J., Volume 34, 353-359, 1993).

Differential diagnosis of NDV involves hemagglutination inhibition with polyclonal NDV-specific antisera (Alexander, 1989, supra; Alexander, 1991, supra), or use of the enzyme-linked imunosorbent assay (ELISA) (Jestin et al., Arch. Virol., Volume 105, 199-208, 1989; Miers et al., Avian Pathol., Volume 27, 1112-1125, 1983; Wilson et al., Avian Dis., Volume 29, 1070-1085, 1984). Oligonucleotide probes (Jarecki-Black et al., Avian Dis., Volume 36, 134-138, 1992; Jarecki-Black et al., Avian Dis., Volume 37, 724-730, 1993) and viral genomic RNA fingerprint analysis (McMillian and Hanson, Avian Dis., Volume 26, 332-339, 1982; Palmieri and Mitchell, Avian Dis., Volume 35, 384-388, 1991) have been used to identify and differentiate NDV strains but with limited success. Monoclonal antibodies are now used to identify antigenic groups but pathotyping NDV isolates involves labor-intensive procedures. Pathotype prediction initially involves NDV inoculation of embryonated eggs to determine the mean time of death of the embryo. Further testing entails inoculation of chickens to determine the intracerebral pathogenicity index and the intravenous pathogenicity index. In the United States, the intracloacal inoculation pathogenicity test is used to distinguish viscerotropic velogenic NDV from neurotropic velogenic viruses. Additionally, virulent NDV can be differentiated by its ability to replicate in most avian and mammalian cell types without the addition of trypsin (Kaleta et al., Comp. Imm. Microbiol. Infect. Dis., Volume 2, 485-496, 1980; King, Avian Dis., Volume 37, 961-969, 1993; Nagai et al., Virology, Volume 72, 494-508, 1976). Although all NDV isolates can replicate in chicken embryo kidney cells, lentogenic viruses require trypsin for replication in avian fibroblasts or mammalian cells (King, supra).

Makkay et al. (Veterinary Microbiology, Volume 66 (3), 209-222, 1999) report that with the advent of subunit vaccines for microbial diseases, it is becoming increasingly important to be able to differentiate naturally infected animals from those vaccinated. Makkay et al. disclose the development of an Enzyme-Linked Immunosorbent Assay (ELISA) using baculovirus-expressed nucleocapsid proteins from Newcastle Disease virus as the coating antigen for a diagnostic and differential ELISA in order to detect antibody to subunit vaccines to Newcastle Disease Virus.

Roehrig et al. (Journal of Clinical Microbiology, Volume 29 (3), 630-631, 1991) disclose the preparation of a murine monoclonal antibody which differentiates between vaccine and wild-type Venezuelan equine encephalomyelitis viruses when used in an ELISA or an ImmunoFlourescent Assay (IFA). The reference discloses that the monoclonal antibody was derived from immunization with a synthetic peptide corresponding to the first 19 amino acids of the E2 glycoprotein of Trinidad donkey Venezuelan equine encephalomyelitis virus.

While methods are available for detecting the presence of NDV in animals, there remains a need for monoclonal antibodies, the hybridomas that produce them, and methods for differentiating high virulent Exotic Newcastle Disease viruses from the low virulent NDV used to produce vaccines of the present invention which overcome some of the limitations of related art detection methods. The present invention described below are novel monoclonal antibodies, novel hybridomas producing the monoclonal antibody, novel peptide sequences used to produce the monoclonal antibodies and methods for using the antibodies and protein.

SUMMARY OF THE INVENTION

It is, therefore, an object of the present invention to provide novel monoclonal antibodies which differentiate between infected animals and vaccinated animals.

It is another object of the present invention to identify novel peptides for making the monoclonal antibodies which can differentiate between animals infected with high virulent Exotic NDV and animals vaccinated with low virulent NDV.

Another object of the present invention is to provide novel hybridomas producing novel monoclonal antibodies which differentiate between animals infected with high virulent Exotic NDV and animals vaccinated with low virulent NDV.

Another object of the present invention is to provide methods for detecting animals that are infected with Newcastle disease virus using a monoclonal antibody that differentiates between a wild type virulent Newcastle Disease Virus and a vaccine Newcastle Disease virus.

A still further object of the present invention is to provide reagents for a commercial diagnostic kit containing a monoclonal antibody capable of differentiating between an animal infected with virulent Newcastle Disease virus and an animal vaccinated for Newcastle Disease virus.

Further objects and advantages of the present invention will become apparent from following description.

DEPOSIT OF THE HYBRIDOMAS

Hybridoma Cell lines: 7F8.C7; 13F7.B6.A7; 10F11.B2.C3; 17F4.F4; 18E9.G3.D7 were submitted on Apr. 17, 2007 and 21A7.B12.F8 submitted on Sep. 20, 2007 for patent deposit purposes on behalf of USDA-ARS Southeast Poultry Research Laboratory. These materials have been deposited under the provisions of the Budapest Treaty with the American Type Tissue Culture Collection (ATCC, Manassas, Va. 20110, USA) on Apr. 17, 2007. The ATCC Patent Deposit Designation PTA-8331, PTA-8332, PTA-8333, PTA-8334, and PTA-8335 for MAb 13F7.B6.A7, 17F4.F4, 10F11.B2.C3, 18E9.G3.D7, and 7F8.C7, respectively. For 21A7.B12.F8, the Deposit Designation is PTA-8641. The deposit has been accepted by the International Depository Authority under the provisions of the Budapest Treaty and all restrictions upon public access to the deposit will be irrevocably removed upon the grant of a patent on this application.

BRIEF DESCRIPTION OF THE DRAWINGS

FIG. 2 shows amino acid alignment of the HN protein from LaSota, B1 and END (California 2002; CA02) viruses. Boxes indicate regions used to produce peptides utilized for immunization of mice.

FIG. 3 shows the amino acid alignment of the P protein from LaSota, B1 and END (California 2002; CA02) viruses. Boxed region indicated region of CA02 sequence used to produce peptides (No 7) for immunization of mice.

FIG. 5 is a photograph of a Dot Blot reactivity of monoclonal antibodies 7F8, 10F11, 13F7, 17F4, 18E9, and 21A7 to NDV antigen. ENDV is Exotic Newcastle Disease Virus (Isolate CA02) and LaSota is a standard NDV vaccine strain.

DETAILED DESCRIPTION OF THE INVENTION

Figure 1:
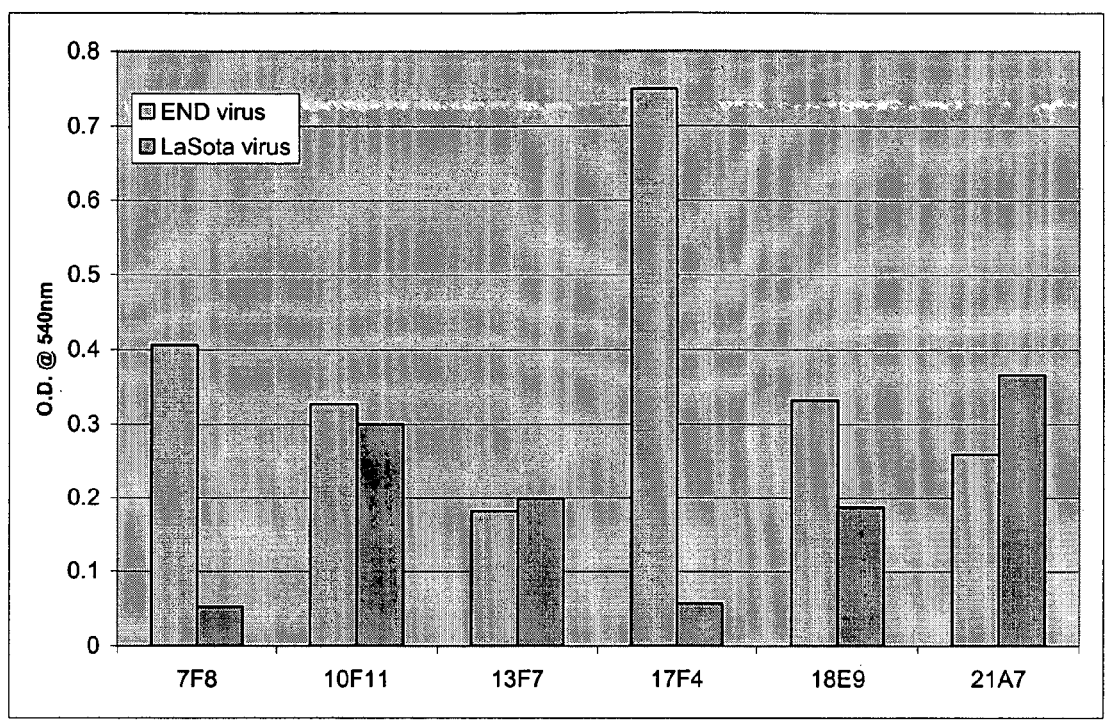
FIG. 1 is a graph showing reactivity of the monoclonal antibodies to the LaSota vaccine strain of NDV and the END virus (California 2002: CA02). A cutoff of about 0.1 O.D. indicates a positive or negative reaction.
Figure 4A:
FIGS. 4a-f show Western blot analysis with anti-peptide monoclonal antibodies 7F8 (FIG. 4a), 10F11 (FIG. 4b), 13F7 (FIG. 4c), 17F4 (FIG. 4d), 18E9 (FIG. 4e) and 21A7 (FIG. 4f) reacting against vaccine NDV HN (SEQ ID NO 2), Exotic NDV HN (SEQ ID NO 5), NDV P (SEQ ID NO 7) or All NDV HN (SEQ ID NO 1) peptide conjugates.
Figure 4B:
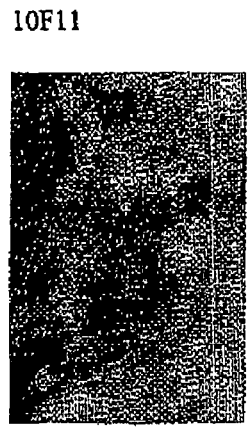
Figure 4C:
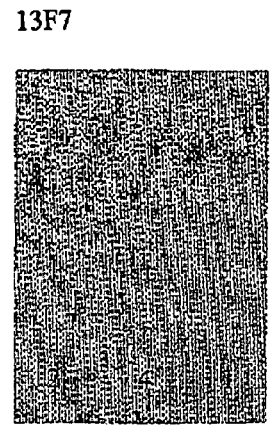
Figure 4D:
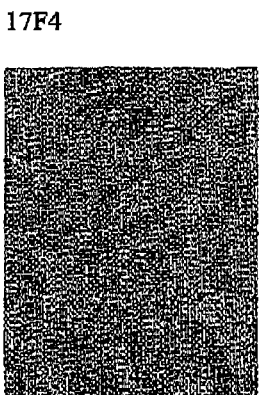
Figure 4E:
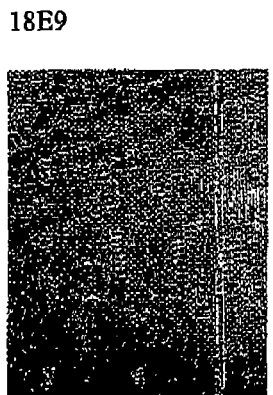
Figure 4F:
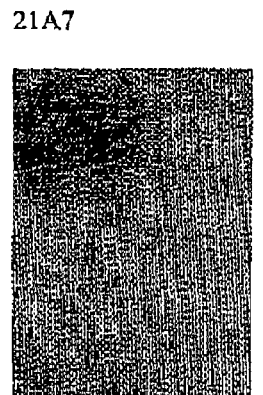

Exotic Newcastle disease (END) is a contagious and fatal viral disease of birds and poultry. On Oct. 1, 2002, END virus (ENDV) was confirmed in commercial poultry operations in California. A quarantine area was imposed over southern California and movement of all poultry and bird species was banned. The ENDV was also isolated in Nevada, Arizona, and Texas. More than 3.4 million birds were depopulated at a cost of more than 200 million dollars in state-federal task force funds. The END outbreak underscores the susceptibility of the poultry industry to Newcastle Disease virus and the need for rapid diagnostic reagents specific for END virus. The present invention is to anti-peptide monoclonal antibodies specific for all NDV and ENDV that can be used for rapid diagnostic identification and detection of END and to the hybridomas and antigens used to produce the monoclonal antibodies. Conventional diagnosis of NDV requires virus isolation and identification of the virus as NDV, which is very time consuming and laborious. The development of a rapid, single-use, field test for ENDV will remove the initial dependence of sample shipping, reduce expenses, and result in faster notification of state and federal officials to the positive identification of an END-infected flock.

Genetic sequence differences between velogenic (highly virulent) and lentogenic (low virulent) isolates were used to develop monoclonal antibodies that detect and differentiate high virulent (exotic) isolates from low virulent (vaccine) isolates.

Seven different peptides were identified to the hemagglutinin-neuraminidase (HN) and Phosphoprotein (P) that allow for specific identification and differentiation of ENDV. The peptides were synthesized, conjugated to Keyhole Limpet Hemocyanin (KLH) and injected into BALB/c mice. Monoclonal antibodies (MAbs) were isolated and tested by Enzyme-Linked Immunosorbent Assay (ELISA) and by Western Blot Analysis with both ENDV and LaSota virus. Final testing was performed using dot blot analysis with ENDV and LaSota virus.

Preparation of hybridomas was accomplished using conventional techniques such as described by Kohler and Milstein (Nature, Volume 256, 495-497, 1975) Koprowski et al. (U.S. Pat. No. 4,196,265) or Wands (U.S. Pat. No. 4,271,145), the contents of which are herein incorporated by reference. Generally, the process of preparation comprises the steps of immunizing an animal with an antigen of interest, recovering splenocytes or lymphocytes from the animal, fusing the splenocytes or lymphocytes with continuously replicating myeloma cells to produce hybrid cells, and screening the resultant hybrid cells for the production of antibodies to the antigen. However, because the peptides of the present invention are relatively small molecules, they are themselves incapable of stimulating the immune system to produce antibodies. To render the compound immunogenic, it must first be conjugated to an immunogenic carrier in such a manner that the resultant immunogen is capable of stimulating the immune system of an animal to produce specific antibodies that are capable of binding the unconjugated peptides of the present invention.

The amino acid sequences of the peptides of the present invention are as follows:

| | |
|---|---|
| MAKSSYKPGRFGGK | SEQ ID NO 1 |
| DGVREARSG | SEQ ID NO 2 |
| EKITSTLG | SEQ ID NO 3 |
| DRVTSLLN | SEQ ID NO 4 |
| QRPTQQQGSQPSR | SEQ ID NO 5 |
| QPLAKQHGNQLNH | SEQ ID NO 6 |
| DRV | SEQ ID NO 7 |

SEQ ID NO 1 sequence is an HN amino acid sequence and is used to produce monoclonal antibodies to detect "all" NDV; SEQ ID NO 2 is an HN amino acid sequence and is used to produce monoclonal antibodies to detect vaccine strains (La-Sota/B1) of NDV; SEQ ID NO 3 is an HN amino acid sequence based on LaSota/B1 isolates; SEQ ID NO 4 is an HN amino acid sequence and is used to produce monoclonal antibodies to detect only END viruses; SEQ ID NO 5 is a P protein amino acid sequence based on LaSota/B1 vaccine strains of NDV; and SEQ ID NO 6 is a P protein amino acid sequence used to produce monoclonal antibodies to detect ENDV/Ca02 isolate.

These peptides are rendered immunogenic by coupling them to an immunogenic carrier by the following procedure. The immunizing agent is constructed by covalently conjugating a peptide of the present invention to an immunogenic carrier protein, preferably by means of a crosslinker, such as a gluteraldehyde moiety. Immunogenic carriers are defined herein as any compound to which any one of the peptides of the present invention may be attached to render the peptide immunogenic. Suitable carriers are well known and may be readily determined by the skilled practitioner in the art. Without being limited thereto, preferred carriers include proteins such as, for example, keyhole limpet hemocyanin (KLH), bovine serum albumin (BSA), ovalbumin (OVA) and human thyroglobulin. The function of the crosslinker is to introduce into the molecule a spacer of sufficient size to prevent the carrier protein from masking the peptide molecule.

To generate antibody-producing splenocytes or lymphocytes, an immunizing preparation comprising the antigen (peptide-carrier conjugate) is injected into an immunologically competent animal. The preparation may also contain other proteins, although pure or substantially pure compositions of the conjugate in a pharmaceutically acceptable carrier are preferred.

Without being limited thereto, rats and particularly mice are preferred hosts for raising antibodies because of ease of handling. BALB/c mice are most commonly used. Preparation of hybridomas using splenocytes from these animals fused to any of a variety of myeloma cell lines, such as SP2/0, is well-known in the literature.

The immunization protocol includes an injection schedule that is sufficient to allow for maturation of the immune response in the animal. Preferably, a series comprising an initial injection followed by about 3-4 boosters at approximately 30-day intervals should be given prior to fusion. The dose of antigen injected should be sufficient to stimulate the immune system. Any reasonable amount in excess of 25 µg per injection would be effective. Typically, the antigen is suspended in a physiological vehicle, such as isotonic saline or Phosphate Buffered Saline (PBS) buffer. In accordance with a preferred embodiment, an adjuvant may be incorporated into the immunizing preparation for enhanced stimulation of the immune system, particularly for the first 1-2 or 1-3 injections. A variety of adjuvants which are conventional in the art may be used herein, although Freund's or RIBI adjuvants are preferred. The route of injection is typically intraperitoneally, though other routes would also likely be effective in inducing an immune response.

Splenocytes or lymphocytes recovered from the immunized animal are fused with continuously replicating tumor cells, such as myeloma or lymphoma cells, cultured and hybridoma cells selected using techniques conventional in the art. Many continuously replicating tumor cell lines are available which may be used as fusion partners with the splenocytes. Without being limited thereto, preferred myeloma cells include P3, NS1, K653, and particularly SP2/0.

Fusion and culture of the cells can be performed using conventional techniques. In accordance with one well known effective procedure, the splenocytes and myeloma cells are fused by exposure to polyethylene glycol. Hybrid cells are selected by culture in hypoxanthine-aminopterin-thymidine (HAT) medium, whereby unfused myeloma cells are killed by HAT and splenocytes die out, leaving only the hybrid cells. The resultant hybridomas are then grown in RPMI or other suitable culture medium and assayed for antibody production.

Samples of the supernatant culture fluid from the hybridomas are screened using a plurality of techniques such as RIA and Enzyme-Linked immunosorbent assay (ELISA), in accordance with the preferred embodiment of the invention, an indirect ELISA is employed. Generally, solid substrates, such as beads or the wells of a microtiter plate, which are coated with the antigen or antigen-conjugate, are used to bind the anti-peptide antibody in the supernatant culture fluid. A preferred coating is BSA-coupled peptide. Detection of bound antibody may be accomplished by addition of enzyme-labeled anti-immunoglobulin antibodies followed by enzyme substrate. Horseradish peroxidase and its substrate, 2,2'-azinobis-3-ethylbenthiazoline-sulfonic acid (ABTS) are preferred enzyme/substrate labels. However, it is understood that other enzyme/substrate labels or non-enzyme labels such as radiolabels or chromophores may also be used.

Cloning of hybridomas which are positive for desired antibody production can be carried out as soon as they are detected by any method known in the art. Hybridomas having a positive response in the ELISA screen are preferably expanded and subcloned one or more times by limiting dilution to assure monoclonality.

The supernatant culture fluid from the cloned hybridomas may also be screened to select for those producing antibodies having a high affinity for the peptides of the present invention. Affinity may be measured using a variety of well known techniques, such as ELISA or RIA. An indirect ELISA was utilized to detect monoclonal binding in these studies. Briefly, the cell-culture supernatant containing monoclonal antibody is added to the wells of an assay plate containing the peptide, conjugated to a different carrier protein than used for injection into the animal. This application ensures antibody reactivity to the peptide and not the carrier protein molecule used for injection. For these studies, KLH was coupled to the peptide to inject into mice, and BSA was coupled to the peptide for testing by ELISA. Following incubation and washing, bound antibody in the wells is detected by the addition of an enzyme-labeled secondary antibody which reacts to the primary monoclonal antibody. The enzyme substrate is added to the wells of the plate and antibody detection is determined colormetrically.

Once hybridomas producing and secreting the desired antipeptide antibodies are identified, large quantities of the antibody(ies) may be produced in tissue culture using well-known techniques. Alternatively, antibody may be produced within host animals, such as by ascites formation in syngenic mice. Monoclonal antibodies so produced may be purified, for example, by affinity chromatography on protein A or G resin, or using peptide bound to a resin.

The antibodies of the present invention may be used to detect exotic Newcastle Disease virus (ENDV) in commercial poultry, as well as low virulent vaccine strains. The antibodies can used to detect ENDV using well known immunoassay procedures including but no limited to radioimmunoassay, ELISA, lateral flow assay, etc.

Lateral flow tests are also known as "dip-stick" or immunochromatographic strip tests. They are a popular platform for rapid tests since their introduction in the late 1980s, and have been designed to detect other virus (e.g. influenza), as well as for home pregnancy tests. Lateral flow tests are used for the specific qualitative or semi-quantitative detection of many analytes including antigens from pathogens, or antibodies against pathogens. Single or multi-analytes can be tested for simultaneously on the same strip. In the case of poultry testing for avian influenza, oral or cloacal swabs are the normal sample applied to the strip, however, in human applications, urine, saliva, serum, plasma, or whole blood can be used as specimens. Test sensitivity and specificity can vary depending on the affinity and avidity of reagents produced. In the case of hepatitis B surface antigen, tests have claimed a sensitivity of 1.0 ng or less. The tests generally use colloidal gold, dye, or latex bead conjugates to generate a signal detectable by the user. An advantage of these types of tests in a diagnostic setting is that they are self contained and do not require specific skills or training to perform or interpret. The assembled strips are prepared, dried and packaged and have a stable shelf-life when properly stored. To perform a test, the sample is placed in extraction or running buffer and placed on the sample pad at one end of the strip. The capture reagent binds to the antigen or antibody in the sample and moves through the strip by capillary action. If specific analyte is present, the signal reagent binds to it, and a second antibody or antigen-immobilized as a line in the nitrocellulose-then captures the complex. If the test is positive, a pink/purple line develops depending on the chromatogen employed in the test strip. Results are generally observed in 5 to 20 minutes. All tests include an internal positive control line that is used to validate the test result. The appearance of two lines, therefore, indicates a positive result, while a negative test produces only a single line.

The monoclonal antibodies and/or peptides of the present invention may be incorporated into lateral flow kits alone, or together with any other necessary reagents. Such a kit for use comprises a first container comprising the monoclonal antibody, a second container comprising a detection reagent effective for detecting bound antibody, and a peptide conjugate of the present invention bound to a solid support.

Detection and differentiation of ENDV from NDV in animal tissue samples, body fluids, excretions or feeds may be performed using the above-described assay with minimal sample preparation and without extensive extraction procedures. Samples need only be placed in appropriate extraction or running buffer and applied to the lateral flow strip.

In an alternative embodiment of this invention, it is understood that antibody fragments having the epitope for recognizing and/or binding a peptide of the present invention could be substituted for the intact immunoglobulin. In illustration, the Fab monovalent fragment can be generated by digestion of the immunoglobulin with papain. The Fab fragments each have a single antigen-binding site. The (Fab')$_2$ bivalent fragment can be generated by digestion of immunoglobulin with pepsin wherein each fragment contains two antigen-binding sites and is still capable of cross-linking antigen. The Fv (variable fragment) can be used for the same purpose as the intact IgG for binding a peptide of the present invention.

Fv is the minimum antibody fragment which contains a complete antigen-recognition and -binding site. In a two-chain Fv species, this region consists of a dimer of one heavy- and one light-chain variable domain in tight, non-covalent association. In a single-chain Fv species (scFv), one heavy- and one light-chain variable domain can be covalently linked by a flexible peptide linker such that the light and heavy chains can associate in a dimeric structure analogous to that in a two-chain Fv species.

The following examples are intended only to further illustrate the invention and are not intended to limit the scope of the invention which is defined by the claims.

EXAMPLE 1

To identify specific peptide sequences, embryo-propagated Newcastle Disease Virus (NDV) for the California 2002-2003 END outbreak isolate (CA02) was purified by density gradient centrifugation and genomic RNA extracted with a commercial RNA extraction kit (Qiagen RNeasy™). Degenerate oligonucleotide primers that recognize NDV genomic sequences were used for RT-PCR amplification of the F and HN genes (Seal et al., J. Clin. Microbiol., Volume 33, 2624-2630, 1995; herein incorporated by reference). Synthesized cDNA was cloned into plasmid vectors (Mead et al., Biotechnology, Volume 9, 657-663, 1991; herein incorporated by reference) and replicated in bacteria (Hanahan, Techniques for transformation of E. coli, IRL Press, Oxford, 1985; herein incorporated by reference). Double-stranded DNA sequencing (Sanger et al., Proc Natl Acad Sci USA, Volume 74, 5463-5467, 1977; herein incorporated by reference) with fluorescently-labeled dideoxynucleotides and Taq polymerase (Applied Biosystems Inc., Foster City, Calif.) was performed with an automated sequencer (Smith et al., Nature, Volume 321, 674-679, 1986) and M13 universal forward and reverse primers. Nucleotide, predicted amino acid sequence analysis, and multiple alignments were performed with the CLUSTAL V™ (Higgins et al., Comput Appl Biosci, Volume 8, 189-191, 1992; herein incorporated by reference) method using LASERGENE™ software version 1.03 (DNASTAR, Madison, Wis.). The HN amino acid sequences from the commonly used NDV vaccine strains, LaSota/B1, were obtained form GenBank (LaSota-AY845400; B1-NC__002617) and aligned (MEGALIGN™) with the CA02 isolate. Peptides specific for CA02 and vaccine strains were identified and analyzed for predicted antigenicity. Peptides were synthesized and coupled to Keyhole Limpet Hemocyanin (KLH) using standard procedures (Sigma-GenoSys™). Based on amino acid alignment (FIGS. 1 and 2) and antigenic index analysis, three different peptides were identified to the HN (Table 1) protein and one to the P protein (Table 2) that would allow for specific detection and differentiation of ENDV from LaSota/B1 vaccine strains.

TABLE 1

Amino acid sequences of HN protein from different NDV strains. Peptides produced to detect all NDV vaccine strains (LaSota/B1) and Exotic strains specific are shown in bold.

| NDV Strain | To detect All NDV Amino Acid position 354-367 | To detect NDV strains Specific Amino Acid position 572-580 | To detect END strain Specific Amino Acid Position 68-75 |
|---|---|---|---|
| LaSota-Vaccine type | MAKSSYKPGRFGGK SEQ ID NO 1 | DGVREARSG SEQ ID NO 2 | EKITSTLG SEQ ID NO 3 |
| B1-Vaccine type | MAKSSYKPGRFGGK SEQ ID NO 1 | DGVREARSG SEQ ID NO 2 | EKITSTLG SEQ ID NO 3 |
| END-Exotic NDV | MAKSSYKPGRFGGK SEQ ID NO 1 | DRV SEQ ID NO 7 | DRVTSLLN SEQ ID NO 4 |
| PEPTIDE PRODUCED | MAKSSYKPGRFGGK SEQ ID NO 1 | DGVREARSG SEQ ID NO 2 | DRVTSLLN SEQ ID NO 4 |

TABLE 2

Amino acid sequences of P protein from different NDV strains. Peptides produced to detect ENDV specific are shown in bold.

| NDV Strain | To detect All NDV Amino Acid position 145-157 |
|---|---|
| LaSota-Vaccine type | QRPTQQQGSQPSR SEQ ID NO 5 |
| B1-Vaccine type | QRPTQQQGSQPSR SEQ ID NO 5 |
| END-Exotic NDV | QPLAKQHGNQLNH SEQ ID NO 6 |
| PEPTIDE PRODUCED | QPLAKQHGNQLNH SEQ ID NO 6 |

EXAMPLE 2

Monoclonal antibodies were produced by immunizing Balb/c mice with an emulsion prepared from KLH-coupled peptide in Freud's complete and incomplete adjuvant for priming and boosting, respectively. Mice were injected intraperitoneally with 0.1 mg of peptide coupled to KLH in complete adjuvant on day 1, 21 and 35. The mice were boosted at day 49 with incomplete adjuvant. Monoclonal antibodies were prepared by fusing spleen cells from peptide-immunized mice with the mouse myeloma cell line SP2/0 in the presence of about 50% polyethylene glycol 1000 (Sigma, St. Louis, Mo.) (Harlow and Lane, Antibodies: a Laboratory Manual, Cold Spring Harbor Laboratory, NY, 1988; herein incorporated by reference). Fused hybridoma cells were resuspended in Iscove's Modified Dulbecco's Medium (Sigma, St. Louis, Mo.) containing hypoxanthine, aminopterin, and thymine (HAT) supplemented with about 20% fetal calf serum in 96-well flat-bottom microtiter plates.

Following growth to about 80% confluency, hybridomas were analyzed for the presence of peptide-specific antibodies by indirect enzyme-linked immunosorbent assay (ELISA) using Bovine Serum Albumin-coupled peptides as antigen. Approximately 50 μl aliquots of cell culture supernatants were transferred to individual wells of a 96-well microtiter plate coated with about 10 μg/ml peptide. Detection was carried out using rabbit anti-mouse immunoglobulin (Ig)G or M conjugated to alkaline pohosphatase (Sigma, St. Louis, Mo.) and substrate containing SigmaFast pNPP tablets (Sigma, St. Louis, Mo.). Individual microtiter plate wells were read at the dual wavelengths of about 405 nm and about 490 nm. Selected monoclonal antibody-secreting hybridoma cell lines were cloned by limiting dilution in microtiter plates.

Isotypes of the monoclonal antibodies were determined using IsoStrip Mouse Monoclonal Antibody Isotyping Kit according to the manufacturer's instructions (Roche Applied Science, Indianapolis, Ind.).

Characterization of monoclonal antibody specificity was examined using CA02 and LaSota virus as antigen. Wells of microtiter plates (Immunlon 2; Dynex, Chantilly, Va.) were coated with approximately 10 μg/ml of betapropiolactone (BPL)-inactivated Newcastle Disease Virus in carbonate coating buffer (pH about 9.6) for approximately 3 hours at room temperature and held overnight at about 4° C. Hybridoma supernatants were diluted 2-fold and reactivity performed in the indirect ELISA as described above in this example. All incubation times were approximately 1 hour and volumes were approximately 50 μl.

In addition, characterization of monoclonal antibody specificity was performed using Western blot analysis. The BSA-coupled NDV amino acid peptides were separated by SDS-PAGE in a 10% polyacrylamide gel using the Bio-Rad Criterion system (Bio-Rad Laboratories, Inc., Hercules, Calif.) (Laemmli et al., J. Mol. Biol., Volume 47, 69-85, 1979; herein incorporated by reference). The separated proteins were transferred onto a 0.45 μM nitrocellulose membrane by semi-dry blot with a Bio-Rad Trans-Blot SD Semi-Dry Cell (Towbin et al., Proc. Natl. Acad.: Sci., USA, Volume 76, 4350-4354, 1979; herein incorporated by reference). Transfer was performed at a constant voltage of approximately 15 volts for about 20 minutes. Following transfer, unbound protein binding sites were blocked by incubation with about 5% skim milk in PBS-T (about 0.05% TWEEN 20 in Phosphate Buffer Solution) for about 1 hour at room temperature. Longitudinal strips were cut and reacted with undiluted hybridoma culture supernatant. Each membrane strip was reacted with secondary antibody (goat anti-mouse IgG or M conjugated to horseradish peroxidase, Southern Biotech Associates, Inc., Birmingham, Ala.) at about a 1:2000 dilution for about 1 hour. The membranes were reacted with ECL Western Blotting Detection Reagents (Amersham Biosciences, Piscataway, N.J.) according to manufacturers' recommendation and exposed to Hyperfilm ECL (Amersham Biosciences). The film was developed using Kodak GBX developing reagents (Eastman Kodak Company, Rochester, N.Y.) according to the manufacturers' recommendations.

The results from the ELISA studies using whole inactivated NDV isolates, ENDV or LaSota, are shown in FIG. 1. Results indicate that all MAb's produced reacted against either ENDV alone or both isolates. MAb's 10F11, 13F7, 18E9 and 21A7 reacted against ENDV and LaSota, while MAb's 7F8 and 17F4 only detected ENDV. Likewise, western blot analysis of the MAb's produced in this invention confirmed reactivity against the peptide used for injection in mice (FIG. 4). MAb 13F7 and 18E9 react against the HN protein to amino acid sequences found in "all" NDV, and were identified as IgG and IgM isotypes, respectively (Table 3). MAb 10F11 reacted against the P protein of NDV, and is an IgM isotype. MAb's 7F8 (IgM) and 17F4 (IgG) reacted against the HN of ENDV only, while 21A7 (IgM) appeared to against peptide SEQ ID NO 2.

TABLE 3

Monoclonal antibodies produced in this invention react against different NDV peptides. Hybridomas were tested and identified by indirect ELISA and Western blot to BSA coupled peptide. Isotypes were determined based on reactivity in a commercial kit.

| React against | MAb Identification | |
|---|---|---|
| ALL NDV HN peptide SEQ ID NO 1 | 13F7 | 18E9 |
| MAb Isotype | IgG | IgM |
| Vaccine strains HN SEQ ID NO 2 | 21A7 | |
| MAb Isotype | IgM | |
| ENDV HN SEQ ID NO 4 | 7F8 | 17F4 |
| MAb Isotype | IgM | IgG |
| NDV P peptide SEQ ID NO 6 | 10F11 | |
| MAb Isotype | IgM | |

EXAMPLE 3

Figure 5:
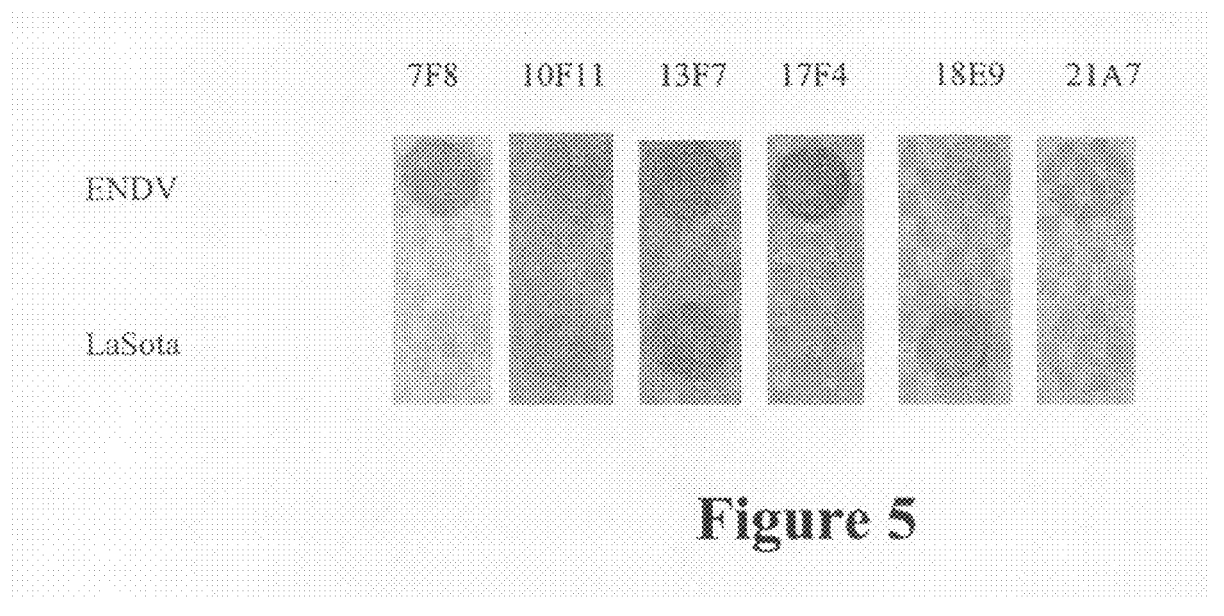

Based on the MAb reactivity profile established above, the reagents were tested on live NDV viruses for detection via Dot Blot analysis (FIG. 5). NDV viruses were grown in 9-11 day-of-embryonation SPF chicken eggs and harvest after 72 hour. Viruses were partially purified (Kapczynski, 2003) and 5 µl spots applied onto nitrocellulose membranes. After drying, the spots were reacted against the MAb's reported here. Results indicate MAb's 7F8 and 17F4 react only against END and not the vaccine strain of NDV. In contrast, MAb's 10F11, 13F7, 18E9 and 21A7 reacted with both ENDV and the LaSota vaccine isolate, indicating they could be used to detect all NDV's in a lateral flow assay. The reaction of MAb 21A7 against ENDV was unexpected based on amino acid sequence, however, a small degree of homology is observed between the NDV isolates, and thus the MAb is believed to be recognizing that conserved epitope. Combining ENDV specific MAb's 7F8 or 17F4 with MAb specific for all strains of NDV would results in a test that could distinguish vaccine strains of NDV from ENDV infected birds.

The foregoing detailed description is for the purpose of illustration. Such detail is solely for that purpose and those skilled in the art can make variations therein without departing from the spirit and scope of the invention.

I claim:

1. An isolated monoclonal antibody or fragment thereof that binds to a peptide consisting of SEQ ID NO 1.

2. An isolated monoclonal antibody or fragment thereof that binds to a peptide consisting of SEQ ID NO 2.

3. An isolated monoclonal antibody or fragment thereof that binds to a peptide consisting of SEQ ID NO 4.

4. An isolated monoclonal antibody or fragment thereof that binds to a peptide consisting of SEQ ID 6.

* * * * *

```
                        SEQUENCE LISTING

<160> NUMBER OF SEQ ID NOS: 13

<210> SEQ ID NO 1
<211> LENGTH: 14
<212> TYPE: PRT
<213> ORGANISM: Newcastle disease virus

<400> SEQUENCE: 1

Met Ala Lys Ser Ser Tyr Lys Pro Gly Arg Phe Gly Gly Lys
1               5                   10

<210> SEQ ID NO 2
<211> LENGTH: 9
<212> TYPE: PRT
<213> ORGANISM: Newcastle disease virus

<400> SEQUENCE: 2

Asp Gly Val Arg Glu Ala Arg Ser Gly
1               5

<210> SEQ ID NO 3
<211> LENGTH: 8
<212> TYPE: PRT
<213> ORGANISM: Newcastle disease virus

<400> SEQUENCE: 3

Glu Lys Ile Thr Ser Thr Leu Gly
1               5

<210> SEQ ID NO 4
<211> LENGTH: 8
<212> TYPE: PRT
<213> ORGANISM: Newcastle disease virus

<400> SEQUENCE: 4

Asp Arg Val Thr Ser Leu Leu Asn
1               5

<210> SEQ ID NO 5
<211> LENGTH: 13
<212> TYPE: PRT
<213> ORGANISM: Newcastle disease virus

<400> SEQUENCE: 5

Gln Arg Pro Thr Gln Gln Gln Gly Ser Gln Pro Ser Arg
1               5                   10

<210> SEQ ID NO 6
<211> LENGTH: 13
```

-continued

```
<212> TYPE: PRT
<213> ORGANISM: Newcastle disease virus

<400> SEQUENCE: 6

Gln Pro Leu Ala Lys Gln His Gly Asn Gln Leu Asn His
1               5                   10

<210> SEQ ID NO 7
<211> LENGTH: 3
<212> TYPE: PRT
<213> ORGANISM: Newcastle disease virus

<400> SEQUENCE: 7

Asp Arg Val
1

<210> SEQ ID NO 8
<211> LENGTH: 571
<212> TYPE: PRT
<213> ORGANISM: Newcastle disease virus

<400> SEQUENCE: 8

Met Asp Arg Val Val Ser Arg Val Val Leu Glu Asn Glu Glu Arg Glu
1               5                   10                  15

Ala Lys Asn Thr Trp Arg Leu Val Phe Arg Val Ala Val Leu Ser Leu
                20                  25                  30

Ile Val Met Thr Leu Ala Ile Ser Val Ala Ala Leu Val Tyr Ser Met
            35                  40                  45

Glu Ala Ser Thr Pro Asn Asp Leu Ala Gly Ile Ser Thr Val Ile Ser
        50                  55                  60

Arg Ala Glu Asp Arg Val Thr Ser Leu Leu Asn Ser Asn Gln Asp Val
65                  70                  75                  80

Val Asp Arg Val Tyr Lys Gln Val Ala Leu Glu Ser Pro Leu Ala Leu
                85                  90                  95

Leu Asn Thr Glu Ser Ile Ile Met Asn Ala Ile Thr Ser Leu Ser Tyr
            100                 105                 110

Gln Ile Asn Gly Ala Ala Asn Ser Ser Gly Cys Gly Ala Pro Val His
        115                 120                 125

Asp Pro Asp Tyr Ile Gly Gly Val Gly Lys Glu Leu Ile Val Asp Asp
    130                 135                 140

Thr Ser Asp Ala Thr Ser Phe Tyr Pro Ser Ala Tyr Gln Glu His Leu
145                 150                 155                 160

Asn Phe Ile Pro Ala Pro Thr Thr Gly Ser Gly Cys Thr Arg Ile Pro
                165                 170                 175

Ser Phe Asp Met Ser Ala Thr His Tyr Cys Tyr Thr His Asn Val Ile
            180                 185                 190

Leu Ser Gly Cys Arg Asp His Ser His Ser His Gln Tyr Leu Ala Leu
        195                 200                 205

Gly Val Leu Arg Thr Ser Ala Thr Gly Arg Val Phe Phe Ser Thr Leu
    210                 215                 220

Arg Ser Ile Asn Leu Asp Asp Thr Gln Asn Arg Lys Ser Cys Ser Val
225                 230                 235                 240

Ser Ala Thr Pro Leu Gly Cys Asp Met Leu Cys Ser Lys Val Thr Glu
                245                 250                 255

Thr Glu Glu Glu Asp Tyr Lys Ser Val Thr Pro Thr Ser Met Val His
            260                 265                 270

Gly Arg Leu Gly Phe Asp Gly Gln Tyr His Glu Lys Asp Leu Asp Val
```

```
                   275                 280                 285
Thr Val Leu Phe Lys Asp Trp Val Ala Asn Tyr Pro Gly Val Gly Gly
    290                 295                 300

Gly Ser Leu Ile Asp Asp Arg Val Trp Phe Pro Val Tyr Gly Gly Leu
305                 310                 315                 320

Lys Pro Asn Ser Pro Ser Asp Thr Ala Gln Glu Gly Lys Tyr Val Ile
                325                 330                 335

Tyr Lys Arg Tyr Asn Asn Thr Cys Pro Asp Glu Gln Asp Tyr Gln Val
            340                 345                 350

Arg Met Ala Lys Ser Ser Tyr Lys Pro Gly Arg Phe Gly Gly Lys Arg
        355                 360                 365

Val Gln Gln Ala Ile Leu Ser Ile Lys Val Ser Thr Ser Leu Gly Glu
    370                 375                 380

Asp Pro Val Leu Thr Val Pro Pro Asn Thr Val Thr Leu Met Gly Ala
385                 390                 395                 400

Glu Gly Arg Ile Leu Thr Val Gly Thr Ser His Phe Leu Tyr Gln Arg
                405                 410                 415

Gly Ser Ser Tyr Phe Ser Pro Ala Leu Leu Tyr Pro Met Thr Val Arg
            420                 425                 430

Asn Lys Thr Ala Thr Leu His Ser Pro Tyr Thr Phe Asn Ala Phe Thr
        435                 440                 445

Arg Pro Gly Ser Val Pro Cys Gln Ala Ser Ala Arg Cys Pro Asn Ser
    450                 455                 460

Cys Ile Thr Gly Val Tyr Thr Asp Pro Tyr Pro Val Val Phe His Arg
465                 470                 475                 480

Asn His Thr Leu Arg Gly Val Phe Gly Thr Met Leu Asp Asn Glu Gln
                485                 490                 495

Ala Arg Leu Asn Pro Val Ser Ala Ile Phe Asp Tyr Thr Ser Arg Ser
            500                 505                 510

Arg Ile Thr Arg Val Ser Ser Thr Thr Lys Ala Ala Tyr Thr Thr
        515                 520                 525

Ser Thr Cys Phe Lys Val Val Lys Thr Asn Lys Val Tyr Cys Leu Ser
    530                 535                 540

Ile Ala Glu Ile Ser Asn Thr Leu Phe Gly Glu Phe Arg Ile Val Pro
545                 550                 555                 560

Leu Leu Val Glu Ile Leu Lys Asp Asp Arg Val
                565                 570

<210> SEQ ID NO 9
<211> LENGTH: 577
<212> TYPE: PRT
<213> ORGANISM: Newcastle disease virus

<400> SEQUENCE: 9

Met Asp Arg Ala Val Ser Gln Val Ala Leu Glu Asn Asp Glu Arg Glu
1               5                   10                  15

Ala Lys Asn Thr Trp Arg Leu Ile Phe Arg Ile Ala Ile Leu Phe Leu
            20                  25                  30

Thr Val Val Thr Leu Ala Ile Ser Val Ala Ser Leu Leu Tyr Ser Met
        35                  40                  45

Gly Ala Ser Thr Pro Ser Asp Leu Val Gly Ile Pro Thr Arg Ile Ser
    50                  55                  60

Arg Ala Glu Glu Lys Ile Thr Ser Thr Leu Gly Ser Asn Gln Asp Val
65                  70                  75                  80
```

```
Val Asp Arg Ile Tyr Lys Gln Val Ala Leu Glu Ser Pro Leu Ala Leu
                85                  90                  95

Leu Lys Thr Glu Thr Thr Ile Met Asn Ala Ile Thr Ser Leu Ser Tyr
            100                 105                 110

Gln Ile Asn Gly Ala Ala Asn Asn Ser Gly Trp Gly Ala Pro Ile His
        115                 120                 125

Asp Pro Asp Tyr Ile Gly Gly Ile Gly Lys Glu Leu Ile Val Asp Asp
    130                 135                 140

Ala Ser Asp Val Thr Ser Phe Tyr Pro Ser Ala Phe Gln Glu His Leu
145                 150                 155                 160

Asn Phe Ile Pro Ala Pro Thr Thr Gly Ser Gly Cys Thr Arg Ile Pro
                165                 170                 175

Ser Phe Asp Met Ser Ala Thr His Tyr Cys Tyr Thr His Asn Val Ile
            180                 185                 190

Leu Ser Gly Cys Arg Asp His Ser His Ser Tyr Gln Tyr Leu Ala Leu
        195                 200                 205

Gly Val Leu Arg Thr Ser Ala Thr Gly Arg Val Phe Phe Ser Thr Leu
    210                 215                 220

Arg Ser Ile Asn Leu Asp Asp Thr Gln Asn Arg Lys Ser Cys Ser Val
225                 230                 235                 240

Ser Ala Thr Pro Leu Gly Cys Asp Met Leu Cys Ser Lys Val Thr Glu
                245                 250                 255

Thr Glu Glu Glu Asp Tyr Asn Ser Ala Val Pro Thr Arg Met Ala His
            260                 265                 270

Gly Arg Leu Gly Phe Asp Gly Gln Tyr His Glu Lys Asp Leu Asp Val
        275                 280                 285

Thr Thr Leu Phe Gly Asp Trp Val Ala Asn Tyr Pro Gly Val Gly Gly
    290                 295                 300

Gly Ser Phe Ile Asp Ser Arg Val Trp Phe Ser Val Tyr Gly Gly Leu
305                 310                 315                 320

Lys Pro Asn Ser Pro Ser Asp Thr Val Gln Glu Gly Lys Tyr Val Ile
                325                 330                 335

Tyr Lys Arg Tyr Asn Asp Thr Cys Pro Asp Glu Gln Asp Tyr Gln Ile
            340                 345                 350

Arg Met Ala Lys Ser Ser Tyr Lys Pro Gly Arg Phe Gly Gly Lys Arg
        355                 360                 365

Ile Gln Gln Ala Ile Leu Ser Ile Lys Val Ser Thr Ser Leu Gly Glu
    370                 375                 380

Asp Pro Val Leu Thr Val Pro Pro Asn Thr Val Thr Leu Met Gly Ala
385                 390                 395                 400

Glu Gly Arg Ile Leu Thr Val Gly Thr Ser His Phe Leu Tyr Gln Arg
                405                 410                 415

Gly Ser Ser Tyr Phe Ser Pro Ala Leu Leu Tyr Pro Met Thr Val Ser
            420                 425                 430

Asn Lys Thr Ala Thr Leu His Ser Pro Tyr Thr Phe Asn Ala Phe Thr
        435                 440                 445

Arg Pro Gly Ser Ile Pro Cys Gln Ala Ser Ala Arg Cys Pro Asn Pro
    450                 455                 460

Cys Val Thr Gly Val Tyr Thr Asp Pro Tyr Pro Leu Ile Phe Tyr Arg
465                 470                 475                 480

Asn His Thr Leu Arg Gly Val Phe Gly Thr Met Leu Asp Gly Val Gln
                485                 490                 495

Ala Arg Leu Asn Pro Ala Ser Ala Val Phe Asp Ser Thr Ser Arg Ser
```

```
                500             505             510
Arg Ile Thr Arg Val Ser Ser Ser Thr Lys Ala Ala Tyr Thr Thr
            515             520             525

Ser Thr Cys Phe Lys Val Val Lys Thr Asn Lys Thr Tyr Cys Leu Ser
    530             535             540

Ile Ala Glu Ile Ser Asn Thr Leu Phe Gly Glu Phe Arg Ile Val Pro
545             550             555             560

Leu Leu Val Glu Ile Leu Lys Asp Asp Gly Val Arg Glu Ala Arg Ser
            565             570             575

Gly

<210> SEQ ID NO 10
<211> LENGTH: 577
<212> TYPE: PRT
<213> ORGANISM: Newcastle disease virus

<400> SEQUENCE: 10

Met Asp Arg Ala Val Ser Gln Val Ala Leu Glu Asn Asp Glu Arg Glu
1               5                   10                  15

Ala Lys Asn Thr Trp Arg Leu Ile Phe Arg Ile Ala Ile Leu Leu Leu
            20                  25                  30

Thr Val Val Thr Leu Ala Thr Ser Val Ala Ser Leu Val Tyr Ser Met
        35                  40                  45

Gly Ala Ser Thr Pro Ser Asp Leu Val Gly Ile Pro Thr Arg Ile Ser
    50                  55                  60

Arg Ala Glu Glu Lys Ile Thr Ser Ala Leu Gly Ser Asn Gln Asp Val
65                  70                  75                  80

Val Asp Arg Ile Tyr Lys Gln Val Ala Leu Glu Ser Pro Leu Ala Leu
                85                  90                  95

Leu Asn Thr Glu Thr Thr Ile Met Asn Ala Ile Thr Ser Leu Ser Tyr
            100                 105                 110

Gln Ile Asn Gly Ala Ala Asn Asn Ser Gly Trp Gly Ala Pro Ile His
        115                 120                 125

Asp Pro Asp Phe Ile Gly Gly Ile Gly Lys Glu Leu Ile Val Asp Asp
    130                 135                 140

Ala Ser Asp Val Thr Ser Phe Tyr Pro Ser Ala Phe Gln Glu His His
145                 150                 155                 160

Asn Phe Ile Pro Ala Pro Thr Thr Gly Ser Gly Cys Ile Arg Ile Pro
                165                 170                 175

Ser Phe Asp Met Ser Ala Thr His Tyr Cys Tyr Thr His Asn Ile Ile
            180                 185                 190

Ser Ser Gly Cys Arg Asp His Ser His Ser Tyr Gln Tyr Leu Ala Leu
        195                 200                 205

Gly Val Leu Arg Thr Ser Ala Thr Gly Arg Ile Phe Phe Ser Thr Leu
    210                 215                 220

Arg Ser Ile Asn Leu Asp Asp Thr Gln Asn Arg Lys Ser Cys Ser Val
225                 230                 235                 240

Ser Ala Thr Pro Leu Gly Cys Asp Met Leu Cys Ser Lys Val Thr Glu
                245                 250                 255

Thr Glu Glu Asp Tyr Asn Ser Ala Val Pro Thr Leu Met Val His
            260                 265                 270

Gly Arg Leu Gly Phe Asp Gly Gln Tyr His Glu Lys Asp Leu Asp Val
        275                 280                 285

Thr Thr Leu Phe Glu Asp Trp Val Ala Asn Tyr Pro Gly Val Gly Gly
```

```
                    290                 295                 300

Gly Ser Phe Ile Asp Ser Arg Val Trp Phe Ser Val Tyr Gly Gly Leu
305                 310                 315                 320

Lys Pro Asn Ser Pro Ser Asp Thr Val Gln Glu Glu Lys Tyr Val Ile
                325                 330                 335

Tyr Lys Arg Tyr Asn Asp Thr Cys Pro Asp Glu Gln Asp Tyr Gln Ile
            340                 345                 350

Arg Met Ala Lys Ser Ser Tyr Lys Pro Gly Arg Phe Gly Gly Lys Arg
        355                 360                 365

Ile Gln Gln Ala Ile Leu Ser Ile Lys Val Ser Thr Ser Leu Gly Glu
    370                 375                 380

Asp Pro Val Leu Thr Val Pro Pro Asn Thr Val Thr Leu Met Gly Ala
385                 390                 395                 400

Glu Gly Arg Ile Leu Thr Val Gly Thr Ser His Phe Leu Tyr Gln Arg
                405                 410                 415

Gly Ser Ser Tyr Phe Ser Pro Ala Leu Leu Tyr Pro Met Thr Val Ser
            420                 425                 430

Asn Lys Thr Ala Thr Leu His Ser Pro Tyr Thr Phe Asn Ala Phe Thr
        435                 440                 445

Arg Pro Gly Ser Ile Pro Cys Gln Ala Ser Ala Arg Cys Pro Asn Ser
    450                 455                 460

Cys Val Thr Gly Tyr Tyr Thr Asp Pro Tyr Pro Leu Ile Phe Tyr Arg
465                 470                 475                 480

Asn His Thr Leu Arg Gly Val Phe Gly Thr Met Leu Asp Gly Glu Gln
                485                 490                 495

Ala Arg Leu Asn Pro Ala Ser Ala Val Phe Asp Ser Thr Ser Arg Ser
            500                 505                 510

Arg Ile Thr Arg Val Ser Ser Ser Thr Lys Ala Ala Tyr Thr Thr
        515                 520                 525

Ser Thr Cys Phe Lys Val Val Lys Thr Asn Lys Thr Tyr Cys Leu Ser
    530                 535                 540

Ile Ala Glu Ile Ser Asn Thr Leu Phe Gly Glu Phe Arg Ile Val Pro
545                 550                 555                 560

Leu Leu Val Glu Ile Leu Lys Asn Asp Gly Val Arg Glu Ala Arg Ser
                565                 570                 575

Gly

<210> SEQ ID NO 11
<211> LENGTH: 571
<212> TYPE: PRT
<213> ORGANISM: Newcastle disease virus

<400> SEQUENCE: 11

Met Asp Arg Ala Val Ser Arg Val Ala Leu Glu Asn Glu Glu Arg Glu
1               5                   10                  15

Ala Lys Asn Thr Trp Arg Phe Val Phe Arg Ile Ala Ile Leu Leu Leu
            20                  25                  30

Ile Val Ile Thr Leu Ala Ile Ser Ala Ala Ala Leu Val Tyr Ser Met
        35                  40                  45

Glu Ala Ser Thr Pro Gly Asp Leu Val Gly Ile Pro Thr Val Ile Ser
    50                  55                  60

Arg Ala Glu Glu Lys Ile Thr Ser Ala Leu Ser Ser Asn Gln Asp Val
65                  70                  75                  80

Val Asp Arg Ile Tyr Lys Gln Val Ala Leu Glu Ser Pro Leu Ala Leu
```

-continued

```
                    85                  90                  95
Leu Asn Thr Glu Ser Val Ile Met Asn Ala Ile Thr Ser Leu Ser Tyr
            100                 105                 110

Gln Ile Asn Gly Ala Ala Asn Asn Ser Gly Cys Gly Ala Pro Val His
            115                 120                 125

Asp Pro Asp Tyr Ile Gly Gly Ile Gly Lys Glu Leu Ile Val Asp Asp
            130                 135                 140

Ala Ser Asp Val Thr Ser Phe Tyr Pro Ser Ala Phe Gln Glu His Leu
145                 150                 155                 160

Asn Phe Ile Pro Ala Pro Thr Thr Gly Ser Gly Cys Thr Arg Ile Pro
                165                 170                 175

Ser Phe Asp Ile Ser Ala Thr His Tyr Cys Tyr Thr His Asn Val Ile
                180                 185                 190

Leu Ser Gly Cys Arg Asp His Ser His Ser His Gln Tyr Leu Ala Leu
                195                 200                 205

Gly Val Leu Arg Thr Ser Ala Thr Gly Arg Val Gly Gly Ser Thr Leu
            210                 215                 220

Arg Ser Ile Asn Leu Asp Asp Asn Gln Asn Arg Lys Ser Cys Ser Val
225                 230                 235                 240

Ser Ala Thr Pro Leu Gly Cys Asp Met Leu Cys Ser Lys Ile Thr Glu
                245                 250                 255

Thr Glu Glu Glu Asp Tyr Ser Ser Val Thr Pro Thr Ser Met Val His
            260                 265                 270

Gly Arg Leu Gly Phe Asp Gly Gln Tyr His Glu Lys Asp Leu Asp Val
            275                 280                 285

Ile Thr Leu Phe Lys Asp Trp Val Ala Asn Tyr Pro Gly Val Gly Gly
            290                 295                 300

Gly Ser Phe Ile Asp Asn Arg Val Trp Phe Pro Val Tyr Gly Gly Leu
305                 310                 315                 320

Lys Pro Asn Ser Pro Ser Asp Thr Val Gln Glu Gly Arg Tyr Val Ile
                325                 330                 335

Tyr Lys Arg Tyr Asn Asp Thr Cys Pro Asp Glu Gln Asp Tyr Gln Ile
            340                 345                 350

Arg Met Ala Lys Ser Ser Tyr Lys Pro Gly Arg Phe Gly Gly Lys Arg
            355                 360                 365

Val Gln Gln Ala Ile Leu Ser Ile Lys Val Ser Thr Ser Leu Gly Glu
            370                 375                 380

Asp Pro Val Leu Thr Ile Pro Pro Asn Thr Val Thr Leu Met Gly Ala
385                 390                 395                 400

Glu Gly Arg Val Leu Thr Val Gly Thr Ser His Phe Leu Tyr Gln Arg
                405                 410                 415

Gly Ser Ser Tyr Phe Ser Pro Ala Leu Leu Tyr Pro Met Thr Val Asn
                420                 425                 430

Asn Lys Thr Ala Thr Leu His Ser Pro Tyr Thr Phe Asn Ala Phe Thr
            435                 440                 445

Arg Pro Gly Ser Val Pro Cys Gln Ala Ser Ala Arg Cys Pro Asn Ser
450                 455                 460

Cys Val Thr Gly Val Tyr Thr Asp Pro Tyr Pro Leu Ile Phe His Arg
465                 470                 475                 480

Asn His Thr Leu Arg Gly Val Phe Gly Thr Met Leu Asp Asp Gly Gln
                485                 490                 495

Ala Arg Leu Asn Pro Val Ser Ala Val Phe Asp Asn Ile Ser Arg Ser
            500                 505                 510
```

```
Arg Ile Thr Arg Val Ser Ser Arg Thr Lys Ala Ala Tyr Thr Thr
            515                 520                 525

Ser Thr Cys Phe Lys Val Val Lys Thr Asn Lys Thr Tyr Val Leu Ser
    530                 535                 540

Ile Ala Glu Ile Ser Asn Thr Leu Phe Gly Glu Phe Arg Ile Val Pro
545                 550                 555                 560

Leu Leu Val Glu Ile Leu Lys Asn Asp Gly Val
                565                 570

<210> SEQ ID NO 12
<211> LENGTH: 577
<212> TYPE: PRT
<213> ORGANISM: Newcastle disease virus

<400> SEQUENCE: 12

Met Asp Arg Thr Val Ser Gln Val Ala Leu Glu Asn Asp Glu Arg Glu
1               5                   10                  15

Ala Lys Asn Thr Trp Arg Leu Ile Phe Arg Ile Ala Ile Leu Leu Leu
            20                  25                  30

Thr Val Val Thr Leu Ala Thr Ser Val Ala Ser Leu Val Tyr Ser Met
        35                  40                  45

Gly Ala Ser Thr Pro Ser Asp Leu Val Gly Ile Pro Thr Arg Ile Ser
    50                  55                  60

Arg Ala Glu Glu Lys Ile Thr Ser Ala Leu Gly Ser Asn Gln Asp Val
65                  70                  75                  80

Val Asp Arg Ile Tyr Lys Gln Val Ala Leu Glu Ser Pro Leu Ala Leu
                85                  90                  95

Leu Asn Thr Glu Thr Thr Ile Met Asn Ala Ile Thr Ser Leu Ser Tyr
            100                 105                 110

Gln Ile Asn Gly Ala Ala Asn Asn Ser Gly Trp Gly Ala Pro Ile His
        115                 120                 125

Asp Pro Asp Phe Ile Gly Gly Ile Gly Lys Glu Leu Ile Val Asp Asp
    130                 135                 140

Ala Ser Asp Val Thr Ser Phe Tyr Pro Ser Ala Phe Gln Glu His Leu
145                 150                 155                 160

Asn Phe Ile Pro Ala Pro Thr Thr Gly Ser Gly Cys Ile Arg Ile Pro
                165                 170                 175

Ser Phe Asp Met Ser Ala Thr His Tyr Cys Tyr Thr His Asn Ile Ile
            180                 185                 190

Ser Ser Gly Cys Arg Asp His Ser His Ser Tyr Gln Tyr Leu Ala Leu
        195                 200                 205

Gly Val Leu Arg Thr Ser Ala Thr Gly Arg Ile Phe Phe Ser Thr Leu
    210                 215                 220

Arg Ser Ile Asn Leu Asp Asp Thr Gln Asn Arg Lys Ser Cys Ser Val
225                 230                 235                 240

Ser Ala Thr Pro Leu Gly Cys Asp Met Leu Cys Ser Lys Val Thr Glu
                245                 250                 255

Thr Glu Glu Glu Asp Tyr Asn Ser Ala Val Pro Thr Leu Met Val His
            260                 265                 270

Gly Arg Leu Gly Phe Asp Gly Gln Tyr His Glu Lys Asp Leu Asp Val
        275                 280                 285

Thr Thr Leu Phe Glu Asp Trp Val Ala Asn Tyr Pro Gly Val Gly Gly
    290                 295                 300

Gly Ser Phe Ile Asp Ser Arg Val Trp Phe Ser Val Tyr Gly Gly Leu
```

```
                305                 310                 315                 320
Lys Pro Asn Ser Pro Ser Asp Thr Val Gln Glu Glu Lys Tyr Val Ile
                325                 330                 335

Tyr Lys Arg Tyr Asn Asp Thr Cys Pro Asp Glu Gln Asp Tyr Gln Ile
                340                 345                 350

Arg Met Ala Lys Ser Ser Tyr Lys Pro Gly Arg Phe Gly Gly Lys Arg
                355                 360                 365

Ile Gln Gln Ala Ile Leu Ser Ile Lys Val Ser Thr Ser Leu Gly Glu
                370                 375                 380

Asp Pro Val Leu Thr Val Pro Pro Asn Thr Val Thr Leu Met Gly Ala
385                 390                 395                 400

Glu Gly Arg Ile Leu Thr Val Gly Thr Ser His Phe Leu Tyr Gln Arg
                405                 410                 415

Gly Ser Ser Tyr Phe Ser Pro Ala Leu Leu Tyr Pro Met Thr Val Ser
                420                 425                 430

Asn Lys Thr Ala Thr Leu His Ser Pro Tyr Thr Phe Asn Ala Phe Thr
                435                 440                 445

Arg Pro Gly Ser Ile Pro Cys Gln Ala Ser Ala Arg Cys Pro Asn Ser
                450                 455                 460

Cys Val Thr Gly Val Tyr Thr Asp Pro Tyr Pro Leu Ile Phe Tyr Arg
465                 470                 475                 480

Asn His Thr Leu Arg Gly Val Phe Gly Thr Met Leu Asp Gly Glu Gln
                485                 490                 495

Ala Arg Leu Asn Pro Ala Ser Ala Val Phe Asp Ser Thr Ser Arg Ser
                500                 505                 510

Arg Ile Thr Arg Val Ser Ser Ser Thr Lys Ala Ala Tyr Thr Thr
                515                 520                 525

Ser Thr Cys Phe Lys Val Val Lys Thr Asn Lys Thr Tyr Cys Leu Ser
                530                 535                 540

Ile Ala Glu Ile Ser Asn Thr Leu Phe Gly Glu Phe Arg Ile Val Pro
545                 550                 555                 560

Leu Leu Val Glu Ile Leu Lys Asn Asp Gly Val Arg Glu Ala Arg Ser
                565                 570                 575

Gly

<210> SEQ ID NO 13
<211> LENGTH: 80
<212> TYPE: PRT
<213> ORGANISM: Newcastle disease virus

<400> SEQUENCE: 13

Gln Ala Thr Ser His Asn Ser Pro Ser Ala Thr Pro Ala Glu Ser Pro
1               5                   10                  15

Pro Thr Gln Ala Ala Gly Glu Ala Gly Asp Thr Gln Leu Lys Thr Gly
                20                  25                  30

Ala Ser Asn Ser Leu Leu Ser Met Leu Asp Lys Leu Ser Asn Lys Ser
            35                  40                  45

Ser Asn Thr Lys Lys Gly Ser Arg Ser Ser Pro Gln Gly Gly His
        50                  55                  60

Gln Pro Leu Ala Lys Gln His Gly Asn Gln Leu Asn His Gly Asn His
65                  70                  75                  80
```